US010451556B2

(12) United States Patent
Robinson et al.

(10) Patent No.: US 10,451,556 B2
(45) **Date of Patent: *Oct. 22, 2019**

(54) METAL-ANTIBODY TAGGING AND PLASMA-BASED DETECTION

(71) Applicant: Purdue Research Foundation, West Lafayette, IN (US)

(72) Inventors: Joseph Paul Robinson, West Lafayette, IN (US); Bartlomiej P. Rajwa, West Lafayette, IN (US); Valery P. Patsekin, West Lafayette, IN (US); Euiwon Bae, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/510,319

(22) PCT Filed: Sep. 14, 2015

(86) PCT No.: PCT/US2015/049916

§ 371 (c)(1),
(2) Date: Mar. 10, 2017

(87) PCT Pub. No.: WO2016/040924

PCT Pub. Date: Mar. 17, 2016

(65) Prior Publication Data

US 2017/0307533 A1 Oct. 26, 2017

Related U.S. Application Data

(60) Provisional application No. 62/049,931, filed on Sep. 12, 2014.

(51) Int. Cl.

*G01N 21/71* (2006.01)
*G01N 33/569* (2006.01)

(Continued)

(52) U.S. Cl.

CPC .......... *G01N 21/718* (2013.01); *G01N 21/25* (2013.01); *G01N 21/67* (2013.01); *G01N 33/569* (2013.01);

(Continued)

(58) Field of Classification Search

CPC ...... G01N 21/718; G01N 21/25; G01N 21/67; G01N 33/58; G01N 33/56911; G01N 33/569

See application file for complete search history.

(56) References Cited

U.S. PATENT DOCUMENTS

| | | |
|---|---|---|
| 5,847,825 A | 12/1998 | Alexander |
| 6,753,957 B1 | 6/2004 | Graft et al. |

(Continued)

FOREIGN PATENT DOCUMENTS

| | | |
|---|---|---|
| WO | WO9945368 | 9/1999 |
| WO | WO2012125652 | 9/2012 |

OTHER PUBLICATIONS

Lou et al., "Polymer-Based Elemental Tags for Sensitive Bioassays", Angew Chem Int Ed Engl., vol. 46, Issue 32, Year: 2007, 4 pages.

(Continued)

*Primary Examiner* — Melanie Brown
(74) *Attorney, Agent, or Firm* — Lee & Hayes, P.C.

(57) ABSTRACT

An apparatus and method for characterizing a target, e.g., microbial samples or biological toxins, includes labeling the target with a biomolecular recognition construct and measuring an atomic-spectra signal of the biomolecular recognition construct. The method can include heating the labeled target before measuring the atomic-spectra signal. The atomic-spectra signal can be measured by performing laser-induced breakdown spectroscopy. The atomic-spectra signal can be measured by performing spark induced breakdown (Continued)

spectroscopy. The biomolecular recognition construct can be prepared by tagging a biological scaffolding with a metal atom or ion. In an aspect in which the target includes a microbial sample, the biological scaffolding can include an antibody against epitopes present on bacterial surface, the antibody linked to a heavy metal. In an aspect in which the target includes a biological toxin, the biological scaffolding can include an antibody against the biological toxin linked to heavy metals.

20 Claims, 10 Drawing Sheets

(51) Int. Cl.
*G01N 33/58* (2006.01)
*G01N 21/67* (2006.01)
*G01N 21/25* (2006.01)

(52) U.S. Cl.
CPC ....... *G01N 33/56911* (2013.01); *G01N 33/58* (2013.01); *G01N 2469/00* (2013.01); *G01N 2469/10* (2013.01)

(56) References Cited

U.S. PATENT DOCUMENTS

| | | | | |
|---|---|---|---|---|
| 9,383,260 | B1 | 7/2016 | Yoo et al. | |
| 2003/0108973 | A1* | 6/2003 | Gatto-Menking ... | G01N 33/543 435/7.93 |
| 2004/0101917 | A1* | 5/2004 | Robey .................... | C12Q 1/689 435/7.32 |
| 2006/0183120 | A1 | 8/2006 | Teh et al. | |
| 2008/0020474 | A1 | 1/2008 | Hayashizaki et al. | |
| 2009/0290151 | A1 | 11/2009 | Agrawal et al. | |
| 2010/0050737 | A1 | 3/2010 | Wolters | |
| 2011/0109904 | A1 | 5/2011 | Ugolin et al. | |
| 2011/0171636 | A1* | 7/2011 | Melikechi ............ | G01N 21/718 435/6.1 |
| 2011/0237446 | A1 | 9/2011 | Treado et al. | |
| 2013/0210165 | A1 | 8/2013 | Meltola et al. | |
| 2014/0287953 | A1 | 9/2014 | Gunther et al. | |
| 2015/0233837 | A1 | 8/2015 | Coulon et al. | |
| 2016/0116415 | A1 | 4/2016 | Gaft et al. | |
| 2016/0161415 | A1 | 6/2016 | Robinson et al. | |

OTHER PUBLICATIONS

Office Action for U.S. Appl. No. 15/042,969, dated Apr. 13, 2018, Robinson, "Metal-Antibody Tagging and Plasma-Based Detection", 14 pages.

Office Action for U.S. Appl. No. 15/042,969, dated Nov. 16, 2017, Robinson, "Metal-Antibody Tagging and Plasma-Based Detection", 9 pages.

Adams, et al., "The Visible Region Absorption Spectra of Rare-Earth Minerals," The American Mineralogist, Mar.-Apr. 1965, vol. 50, pp. 356-366.

Angelo, et al., "Multiplexed ion beam imaging of human breast tumors", Nature Medicine, Epub Mar. 2, 2014, 20(4):436-42, pp. 1-2; fig 1.

Ashley, K., et al., "Interlaboratory Evaluatioin of Trace Element Determination in Workplace Air Filter Samples by Inductively Coupled Plasma Mass Spectrometry", Journal of Environmental Monitoring, 2012, vol. 14, 8 pages.

Bendall, et al., "Single-Cell Mass Cytometry of Differential Immune and Drug Responses Across a Human Hematopoietic Continuum," Science, May 6, 2011, vol. 332, pp. 687-696.

Benoist, et al., "Flow Cytometry, Amped up," Science, May 6, 2011, vol. 332, pp. 677-678.

Bings, et al., "Atomic Spectroscopy: A Review," Analytical Chemistry, Jun. 15, 2010, vol. 82, No. 12, pp. 4653-4681.

Cheng, et al., "Detection of Botulinum Neurotoxin Serotypes A and B Using a Chemiluminescent Versus Electrochemiluminescent Immunoassay in Food and Serum," Journal of Agricultural and Food Chemistry, 2013, vol. 61, pp. 755-760.

Diwakar, P. et al., "Laser-Induced Breakdown Spectroscopy for Analysis of Micro and Nanoparticles", Journal of Analytical Atomic Spectrometry, 2012, vol. 27, 10 pages.

Dixon, et al., "Feasibility of Detection and Identification of Individual Bioaerosols Using Laser-Induced Breakdown Spectroscopy," Analytical Chemistry, Jan. 15, 2005, vol. 77, No. 2, pp. 631-638.

Giesen, et al., "Highly Multiplexed Imaging of Tumor Tissues with Subcellular Resolution by Mass Cytometry," Nature Methods, Apr. 2014, vol. 11, No. 4, 9 pages.

He, et al., "Development and Characterization of Monoclonal Antibodies Against Shiga Toxin 2 and Their Application for Toxin Detection in Milk," Journal of Immunological Methods, 2013, vol. 389, pp. 18-28.

Hunter, et al., "Rapid Field Screening of Soils for Heavy Metals with Spark-Induced Breakdown Spectroscopy," Applied Optics, Apr. 20, 2003, vol. 42, No. 2, pp. 2102-2109.

Majonis, D., et al., "Synthesis of a Functional Metal-Chelating Polymer and Steps Towards Quantitative Mass Cytometry Bioassays," National Institue of Health—Public Access Author Manuscript, Nov. 1, 2010, 82(21), 20 pages.

Mohaidat, et al., "The Effect of Bacterial Environmental and Metabolic Stresses on a Laser-Induced Breakdown Spectroscopy (LIBS) Based Identification of *Escherichia coli* and *Streptococcus viridans*," Applied Spectroscopy, 2001, vol. 65, No. 4, pp. 386-392.

Multari, et al., "Detection of Biological Contaminants on Foods and Food Surfaces Using Laser-Induced Breakdown Spectroscopy (LIBS)," Journal of Agriculture and Food Chemistry, 2013, vol. 61, pp. 8687-8694.

Multari, et al., "Detection of Pesticides and Dioxins in Tissue Fats and Rendering Oils Using Laser-Induced Breakdown Spectroscopy (LIBS)," Journal of Agricultural and Food Chemistry, 2013, vol. 61, pp. 2348-2357.

PCT Search Report and Written Opinion dated Dec. 11, 2015 for PCT Application No. PCT/US15/49916, 6 pages.

Schmidt, et al., "Spark-Induced Breakdown Spectroscopy and Multivariate Analysis Applied to the Measurement of Total Carbon in Soil," Applied Optics, Mar. 1, 2012, vol. 51, No. 7, pp. B176-B182.

Extended European Search Report dated Mar. 9, 2018 for European Patent Application No. 15840345.1, 13 pages.

Rehse, et al., "Identification and discrimination of Pseudomonas aeruginosa bacteria grown in blood and bile by laser-induced breakdown spectroscopy", Spectrochimica Acta, Part B, Atomic Spectroscopy, New York, NY, US vol. 16, No. 10, Sep. 26, 1997, pp. 1169-1176.

Kisker, "Particles—Silica-/Glas-/ Biodegradable Particles", retrieved Feb. 8, 2018, from <<https://www.kisker-biotech.com/frontoffice/product?produitId=K10A-10-01>>, 3 pages.

University of Wisconsin—Madison, "DPTA—Virtual Museum of Molecules and Minerals", retrieved Feb. 9, 2018 from <<https://virtual-museum.sois.wisc.edu/display/dtpa/>>, 1 page.

Office Action for U.S. Appl. No. 15/042,969, dated Apr. 29, 2019, Robinson, "Metal-Antibody Tagging and Plasma-Based Detection", 20 pages.

* cited by examiner

METAL-ANTIBODY TAGGING AND PLASMA-BASED DETECTION

CROSS-REFERENCE TO RELATED APPLICATIONS

The present application is a national stage application of International Patent Application No. PCT/US15/49916, filed Sep. 14, 2015, which is related to and claims the priority benefit of U.S. Provisional Patent Application Ser. No. 62/049,931, filed Sep. 12, 2014, the contents of which are hereby incorporated by reference in their entirety into this disclosure.

STATEMENT OF FEDERALLY SPONSORED RESEARCH OR DEVELOPMENT

This invention was made with government support under Contract No. 59-1935-2-279 awarded by the United States Department of Agriculture. The government has certain rights in the invention.

TECHNICAL FIELD

The present disclosure generally relates to biological detection, and in particular to detection of biological pathogens using antibody tagging.

BACKGROUND

This section introduces aspects that may help facilitate a better understanding of the disclosure. Accordingly, these statements are to be read in this light and are not to be understood as admissions about what is or is not prior art.

The fields of microbiology, biosafety and biosurveillance employ multiple detection technologies paired with various reporting modalities. The most common approaches use traditional optical labeling techniques such as fluorescence, phosphorescence or formation of color chromophores. The optical labels are typically connected to molecular recognition molecules such as antibodies.

Other lesser-known methods for pathogen recognition and/or detection include detection of antibody immobilized bacteria using surface plasmon resonance (SPR) sensors, interferometric biosensors, acoustic wave biosensor platforms based on the thickness shear mode (TSM) resonator, and piezoelectric-excited millimeter-sized cantilever (PEMC) sensors. There has been also experimental work reported on detection involving microfluidic microchips coated with antibodies. The chips have an electric current passed through them. When the chip surface comes into contact with bacteria, the system shows changes in potentiometric, amperometric or impedimetric/conductimetric characteristics demonstrating bacterial presence.

Most of the listed techniques do not offer good multiplexing capability, as they are specifically designed to announce the presence of a specific type or category of bacteria. They are also not easily extendable to detect other biological hazards, such as present of biological toxins. Therefore, improvements are needed in the field.

SUMMARY

In one aspect, a method for characterizing a biological target, is disclosed, the method comprising labeling the target with a biomolecular recognition construct and measuring an atomic-spectra signal of the biomolecular recognition construct. The labeled target may be heated before measuring the atomic-spectra signal. The atomic-spectra signal may be measured by performing laser-induced breakdown spectroscopy. The atomic-spectra signal may also be measured by performing spark induced breakdown spectroscopy. The biomolecular recognition construct may be formed by tagging a biological scaffolding with a metal atom or ion. The target may include a microbial sample and the biological scaffolding may comprise an antibody against epitopes present on bacterial surface, the antibody linked to a heavy metal.

Figure 1:
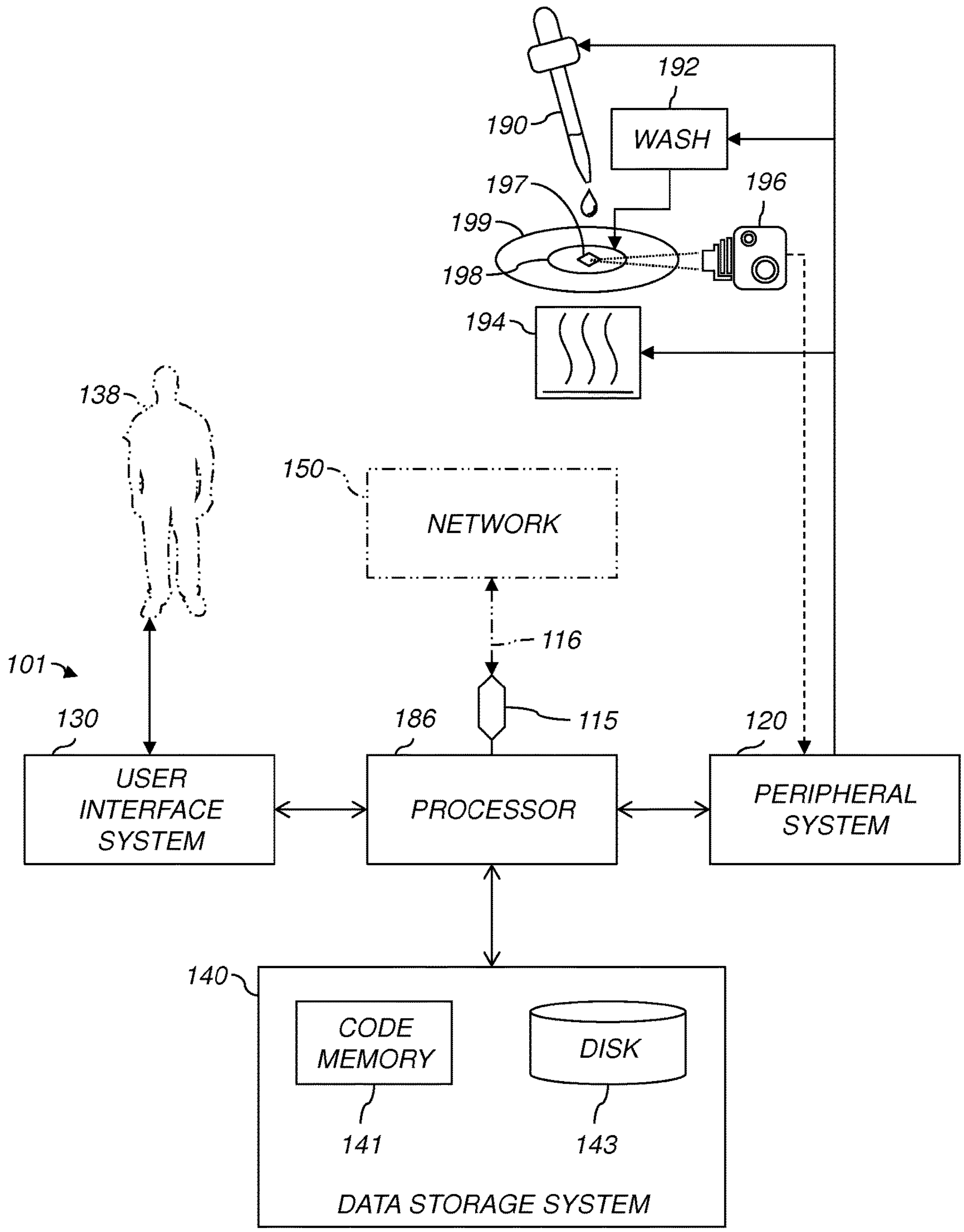
FIG. 1 is a diagram showing the components of a system for detecting a biological target in a sample.

The attached figures are for purposes of illustration and are not necessarily to scale.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The present disclosure provides a method and apparatus for metal-antibody tagging and plasma-based detection (MAPD) which involves the use of metal-labeled recognition macromolecules to tag infectious agents (such as bacterial cells) or toxic biological products and substances (e.g. Ricin, mycotoxins, bacterial toxins, Shiga toxin, Botulinum) for subsequent detection using laser-induced breakdown spectroscopy (LIBS), spark induced breakdown spectroscopy (SIBS), laser ablation molecular isotopic spectrometry (LAMIS) or other detection modalities relying on atomic spectra evaluation after plasma formation.

Various herein-described detection techniques use atomic optical emission spectroscopy. They employ a laser and a focusing lens (LIBS and LAMIS), or a spark (SIBS) to generate a plasma from the vaporized tagged sample.

Some aspects herein are described in terms that can be implemented as software programs. The equivalent of such software can also be constructed in hardware, firmware, or micro-code. Because data-manipulation algorithms and systems are well known, the present description is directed in particular to algorithms and systems forming part of, or cooperating more directly with, systems and methods described herein. Other aspects of such algorithms and systems, and hardware or software for producing and otherwise processing signals or data involved therewith, not specifically shown or described herein, are selected from such systems, algorithms, components, and elements known in the art. Given the systems and methods as described herein, software not specifically shown, suggested, or described herein that is useful for implementation of any aspect is conventional and within the ordinary skill in such arts.

FIG. 1 is a diagram showing the components of an exemplary recognition system 101 for analyzing sample data and performing other analyses described herein, and related components. The system 101 includes a processor 186, a peripheral system 120, a user interface system 130, and a data storage system 140. The peripheral system 120, the user interface system 130 and the data storage system 140 are communicatively connected to the processor 186. Processor 186 can be communicatively connected to network 150 (shown in phantom), e.g., the Internet or a leased line, as discussed below. Lasers, sample addition devices, substrate handlers, and other devices herein can each include one or more processor(s) 186 or one or more of systems 120, 130, 140, and can each connect to one or more network(s) 150. Processor 186, and other processing devices described herein, can each include one or more microprocessors, microcontrollers, field-programmable gate arrays (FPGAs), application-specific integrated circuits (ASICs), programmable logic devices (PLDs), programmable logic arrays (PLAs), programmable array logic devices (PALs), or digital signal processors (DSPs).

Processor 186 can implement processes of various aspects described herein. Processor 186 and related components can, e.g., carry out processes for performing assays using recognition macromolecules as described in Paper 1.

Processor 186 can be or include one or more device(s) for automatically operating on data, e.g., a central processing unit (CPU), microcontroller (MCU), desktop computer, laptop computer, mainframe computer, personal digital assistant, digital camera, cellular phone, smartphone, or any other device for processing data, managing data, or handling data, whether implemented with electrical, magnetic, optical, biological components, or otherwise.

The phrase "communicatively connected" includes any type of connection, wired or wireless, for communicating data between devices or processors. These devices or processors can be located in physical proximity or not. For example, subsystems such as peripheral system 120, user interface system 130, and data storage system 140 are shown separately from the processor 186 but can be embodied or integrated completely or partially within the processor 186. In an example, processor 186 includes an ASIC including a central processing unit connected via an on-chip bus to one or more core(s) implementing function(s) of systems 120, 130, or 140.

The peripheral system 120 can include or be communicatively connected with one or more devices configured or otherwise adapted to provide digital content records to the processor 186 or to take action in response to signals or other instructions received from processor 186. For example, the peripheral system 120 can include digital still cameras, digital video cameras, spectroscopic detector 196, or other data processors. The processor 186, upon receipt of digital content records from a device in the peripheral system 120, can store such digital content records in the data storage system 140.

Processor 186 can, via peripheral system 120, control subsystems 190, 192, 194, and spectroscopic detector 196. Biological sample 198 is carried on substrate 199, which can be, e.g., a silicon (Si) wafer. Target 197 is shown in sample 198 for illustration. Sample 198 can include liquid, gas, powder, bulk solid, or any combination or mixture thereof. Substrate 199 can be manipulated by a wafer-handling or other motion subsystem (not shown). Subsystem 190 (graphically represented as an eyedropper) is configured or otherwise adapted to add a biomolecular recognition construct to the sample 198, e.g., a dispenser or sample-deposition device such as those used in automatic dry- or wet-slide bioassays or in flow cytometry. Subsystem 192 is configured to wash unbound recognition construct out of the sample 198. Subsystem 194 is configured to heat the sample-construct mixture so that metals in the biomolecular recognition construct in the washed sample emit photons at characteristic wavelengths. This subsystem 194 can include a laser, e.g., of a type used in laser-induced breakdown spectroscopy (LIBS). Subsystem 194 can also include a spark induced breakdown spectroscopy (SIBS) spark generator, e.g., a closely-spaced electrode pair connected to a high-voltage power supply so that a high voltage can be introduced across the electrodes to produce a spark. Spectroscopic detector 196 (depicted as a camera; dashed-line connector used for clarity only) is configured to detect light emitted by the metals, e.g., by metal atoms or ions in the recognition macromolecules. In this example, apparatus for detecting a target 197 in a sample 198 includes subsystem 190 for adding a biomolecular recognition construct to the sample, subsystem 192 for washing unbound recognition construct out of the sample, subsystem 194 for ionizing the sample-construct mixture into a plasma. The plasma signal emitted by atomic and ionic species of the metals used to tag the antibodies attached to the sample can be collected by a spectrometer. Sample emits photons at characteristic wavelengths, and spectroscopic detector 196 is used for detecting photons emitted by the metal ions. The plasma generation subsystem 194 can include a laser, or can include at least two electrodes and a high-voltage power supply connected to the at least two electrodes and configured to selectively produce a spark across the at least two electrodes.

The user interface system 130 can convey information in either direction, or in both directions, between a user 138 and the processor 186 or other components of system 101. The user interface system 130 can include a mouse, a keyboard, another computer (connected, e.g., via a network or a null-modem cable), or any device or combination of devices from which data is input to the processor 186. The user interface system 130 also can include a display device, a processor-accessible memory, or any device or combination of devices to which data is output by the processor 186.

The user interface system 130 and the data storage system 140 can share a processor-accessible memory.

In various aspects, processor 186 includes or is connected to communication interface 115 that is coupled via network link 116 (shown in phantom) to network 150. For example, communication interface 115 can include an integrated services digital network (ISDN) terminal adapter or a modem to communicate data via a telephone line; a network interface to communicate data via a local-area network (LAN), e.g., an Ethernet LAN, or wide-area network (WAN); or a radio to communicate data via a wireless link, e.g., WIFI or GSM (Global System for Mobile Communications). Communication interface 115 can send and receives electrical, electromagnetic or optical signals that carry digital or analog data streams representing various types of information across network link 116 to network 150. Network link 116 can be connected to network 150 via a switch, gateway, hub, router, or other networking device.

In various aspects, system 101 can communicate, e.g., via network 150, with other data processing system(s) (not shown), which can include the same types of components as system 101 but is not required to be identical thereto. System 101 and other systems not shown communicatively connected via the network 150. System 101 and other systems not shown can execute computer program instructions to measure constituents of samples or exchange spectra or other data, e.g., as described herein.

Processor 186 can send messages and receive data, including program code, through network 150, network link 116 and communication interface 115. For example, a server can store requested code for an application program (e.g., a JAVA applet) on a tangible non-volatile computer-readable storage medium to which it is connected. The server can retrieve the code from the medium and transmit it through network 150 to communication interface 115. The received code can be executed by processor 186 as it is received, or stored in data storage system 140 for later execution.

Data storage system 140 can include or be communicatively connected with one or more processor-accessible memories configured or otherwise adapted to store information. The memories can be, e.g., within a chassis or as parts of a distributed system. The phrase "processor-accessible memory" is intended to include any data storage device to or from which processor 186 can transfer data (e.g., using components of peripheral system 120). A processor-accessible memory can include one or more data storage device(s) that are volatile or nonvolatile, that are removable or fixed, or that are electronic, magnetic, optical, chemical, mechanical, or otherwise. Exemplary processor-accessible memories include but are not limited to: registers, floppy disks, hard disks, tapes, bar codes, Compact Discs, DVDs, read-only memories (ROM), erasable programmable read-only memories (EPROM, EEPROM, or Flash), and random-access memories (RAMs). One of the processor-accessible memories in the data storage system 140 can be a tangible non-transitory computer-readable storage medium, i.e., a non-transitory device or article of manufacture that participates in storing instructions that can be provided to processor 186 for execution.

In an example, data storage system 140 includes code memory 141, e.g., a RAM, and disk 143, e.g., a tangible computer-readable rotational storage device or medium such as a hard drive. In this example, computer program instructions are read into code memory 141 from disk 143. Processor 186 then executes one or more sequences of the computer program instructions loaded into code memory 141, as a result performing process steps described herein. In this way, processor 186 carries out a computer implemented process. For example, steps of methods described herein, blocks of block diagrams herein, and combinations of those, can be implemented by computer program instructions. Code memory 141 can also store data.

Various aspects described herein may be embodied as systems or methods. Accordingly, various aspects herein may take the form of an entirely hardware aspect, an entirely software aspect (including firmware, resident software, micro-code, etc.), or an aspect combining software and hardware aspects These aspects can all generally be referred to herein as a "service," "circuit," "circuitry," "module," or "system."

Furthermore, various aspects herein may be embodied as computer program products including computer readable program code ("program code") stored on a computer readable medium, e.g., a tangible non-transitory computer storage medium or a communication medium. A computer storage medium can include tangible storage units such as volatile memory, nonvolatile memory, or other persistent or auxiliary computer storage media, removable and non-removable computer storage media implemented in any method or technology for storage of information such as computer-readable instructions, data structures, program modules, or other data. A computer storage medium can be manufactured as is conventional for such articles, e.g., by pressing a CD-ROM or electronically writing data into a Flash memory. In contrast to computer storage media, communication media may embody computer-readable instructions, data structures, program modules, or other data in a modulated data signal, such as a carrier wave or other transmission mechanism. As defined herein, "computer storage media" do not include communication media. That is, computer storage media do not include communications media consisting solely of a modulated data signal, a carrier wave, or a propagated signal, per se.

The program code can include computer program instructions that can be loaded into processor 186 (and possibly also other processors), and that, when loaded into processor 486, cause functions, acts, or operational steps of various aspects herein to be performed by processor 186 (or other processor). The program code for carrying out operations for various aspects described herein may be written in any combination of one or more programming language(s), and can be loaded from disk 143 into code memory 141 for execution. The program code may execute, e.g., entirely on processor 186, partly on processor 186 and partly on a remote computer connected to network 150, or entirely on the remote computer.

In various aspects, a method for characterizing a target, e.g., microbial samples or biological toxins, includes labeling the target with a biomolecular recognition construct and measuring an atomic-spectra signal of the biomolecular recognition construct. The method can include heating the labeled target before measuring the atomic-spectra signal. The atomic-spectra signal can be measured by performing laser-induced breakdown spectroscopy (LIBS). The atomic-spectra signal can be measured by performing spark induced breakdown spectroscopy (SIBS). Data of the atomic-spectra signal can be classified using a computer-based classifier and a classification score can be assigned to the analyzed sample (e.g., spectral unmixing or spectral fingerprint classification).

Using the system 101, the biomolecular recognition construct can be prepared by tagging a biological scaffolding with a metal atom or ion. The biological scaffolding may comprise adNectins, iMabs, anticalins, microbodies, peptide aptamers, designed ankyrin repeat proteins (DARPins), affilins, tentranectins, avimers or other scaffolds. In an aspect in which the target includes a microbial sample, the biological scaffolding can include an antibody against epitopes present on bacterial surface, said antibody linked to a heavy metal. In an aspect in which the target includes a biological toxin, the biological scaffolding can include an antibody against the biological toxin linked to heavy metals.

The scaffold for the molecular recognition system may be tagged using various metallic elements such as Al, Ca, Cr, Cu, Fe, Mg, Mn, Pb, Si, Ti, V and Zn. However, in order to minimize the background it is advisable to use lanthanide metals (rare earth elements) which are typically not present in biological material such as La, Ce, Pr, Nd, Pm, Sm, Eu, Gd, Tb, Dy, Ho, Er, Tm, Yb, and Lu. The probes can be prepared by coupling the scaffolding for molecular recognition to polymers equipped with metal-binding ligands. These polymers contain a functional group enabling them to be covalently attached to biological macromolecules such as antibodies, while simultaneously binding to one or more metals, e.g., metal atoms or ions. We have preformed preliminary studies and propose to extend the use of lanthanide metals (rare earth elements), which are typically not present in biological material (La, Ce, Pr, Nd, Pm, Sm, Eu, Gd, Tb, Dy, Ho, Er, Tm, Yb, and Lu). However, MEPS can be also employed with chelated heavy metal ions, assuming that food contamination by heavy metals is not the target of the specific test. The MEPS probes are prepared by coupling the scaffolding for molecular recognition to polymers equipped with metal-binding ligands. These specially designed polymers contain a functional group enabling them to be covalently attached to biological macromolecules, while simultaneously binding multiple ions of metals. Specifically we have tested antibodies tagged via a reaction involving selective reduction of disulfide bonds in their hinge region, followed by thiol addition to a maleimide group at one end of the MCP. Owing to unique and distinguishable atomic spectral signals from many other metals, MEPS can also take advantage of alternative non-MCP labeling strategies, for example using HgS nanoparticles, silver nanoparticles, organic mercury compounds, or ruthenium compounds. Additionally ions derived from cadmium, mercury, cobalt, arsenic, copper, chromium and selenium can also be identified.

The prepared recognition biomolecular recognition constructs (macromolecules) are subsequently used to perform the assay. There are many possible ways for the recognition biomolecular recognition construct to be used. In one example, a biological specimen containing pathogens or toxins can be attached to an inert surface (e.g. such as a silicon wafer). A metal-tagged antibody or an alternative molecular recognition scaffold is applied over the surface binding to the exposed antigens. The excess antibody or other recognition macromolecule is removed by washing the substrate In another example, in an indirect setting following the attachment of the bacteria cells or toxin macromolecules to the surface of the inert sample holder a primary antibody or other recognition macromolecule is added, binding specifically to the antigens of interest. This primary molecular recognition system is not tagged, in contrast to the reagents described above. Subsequently a secondary (metal-tagged) macromolecule is added binding to the primary macromolecule.

In a further example, an inert surface is functionalized and covered with recognition macromolecules. The biological specimen is added and the antigens of interest are captured by the surface-bound recognition macromolecules. In the last step, the metal-tagged recognition macromolecules are added binding to the immobilized antigen. The excess unbound macromolecules are removed by a wash.

Following the tagging step in these and other aspects, the specimen containing the sample of interest labeled by metal-tagged recognition molecules is analyzed using system 101 by employing one of the atomic spectroscopy techniques mentioned above. In an aspect using LIBS spectroscopy, subsystem 194 focuses a laser beam onto the inert surface (e.g., the silicon wafer) where the sample 198 is deposited. Owing to the large power density of the laser the tagged material starts to evaporate leading to the generation of plasma. The chemical constituents of the biological material are excited by the laser beam and emit radiation which is element specific, upon which the radiation is analyzed by subsystem 196.

In the described settings, simultaneous (multiplexed) analysis of many targets 197 within the sample 198 is possible by utilizing a cocktail of recognition macromolecules (e.g., a mixture of antibodies), each class of recognition macromolecules labeled with a different metal. Owing to distinguishability and specificity of atomic spectra produced by different metals, this tagging arrangement permits effective multiplexing, i.e., simultaneous detection of multiple targets (for instance, different bacterial pathogens or toxins).

The plasma signal emitted by atomic and ionic species of the metals used to tag the antibodies attached to the sample can be collected using a spectrometer, such as subsystem 196. The naturally occurring chemical constituents of the biological sample 198 can also contribute to the atomic spectra signal. In fact, it has been disclosed and demonstrated that the LIBS signal from bacteria alone may lead to recognition of some bacterial species. However, owing to a high similarity in biochemical composition of bacterial species, the classification ability of the label-free methods is relatively low. The spectra are used to determine the elemental constituents of the sample 198, and such constituents are similar for many bacteria or other targets. In various aspects, since the metals used to label the antibodies are either not naturally present in the tested sample 198 of interest or present only in very small quantities, the detection of the spectra of those metals is a direct indicator of a sample type and origin.

Various aspects include digitization of the recorded spectra, followed by spectral unmixing (allowing for the determination of the individual spectral constituents) or spectral fingerprint classification (involving matching the obtained spectrum to other spectra present in the database).

The disclosed system 101 therefore offers faster and more sensitive detection with reduced sample processing and preparation compared to prior art schemes. The presently disclosed detection format allows for multiplexing, e.g. simultaneous detection of multiple bacterial species, biological toxins, or other targets.

Figure 2:
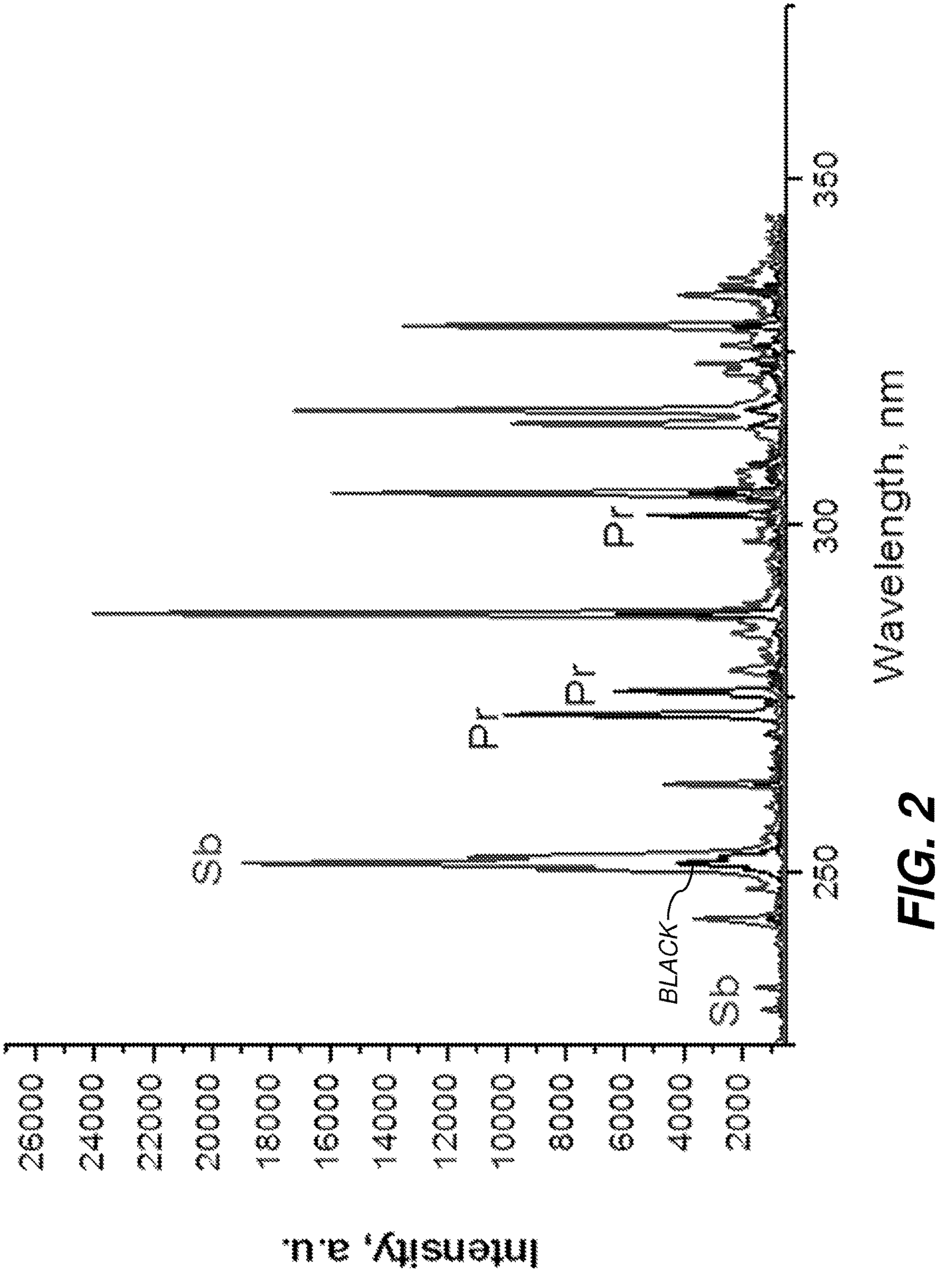
FIG. 2 is a plot showing exemplary data that were collected in an experiment that where samples containing bacteria were labeled with two different metal-tagged antibodies, Sb and Pr according to one embodiment.

In one example, shown in FIG. 2, samples containing bacteria were labelled with two different types of antibodies. The Sb-tagged antibodies (indicated by Sb) attached to *E. coli* can be readily distinguished from Pr-tagged antibodies (indicated by Pr).

Figure 3:
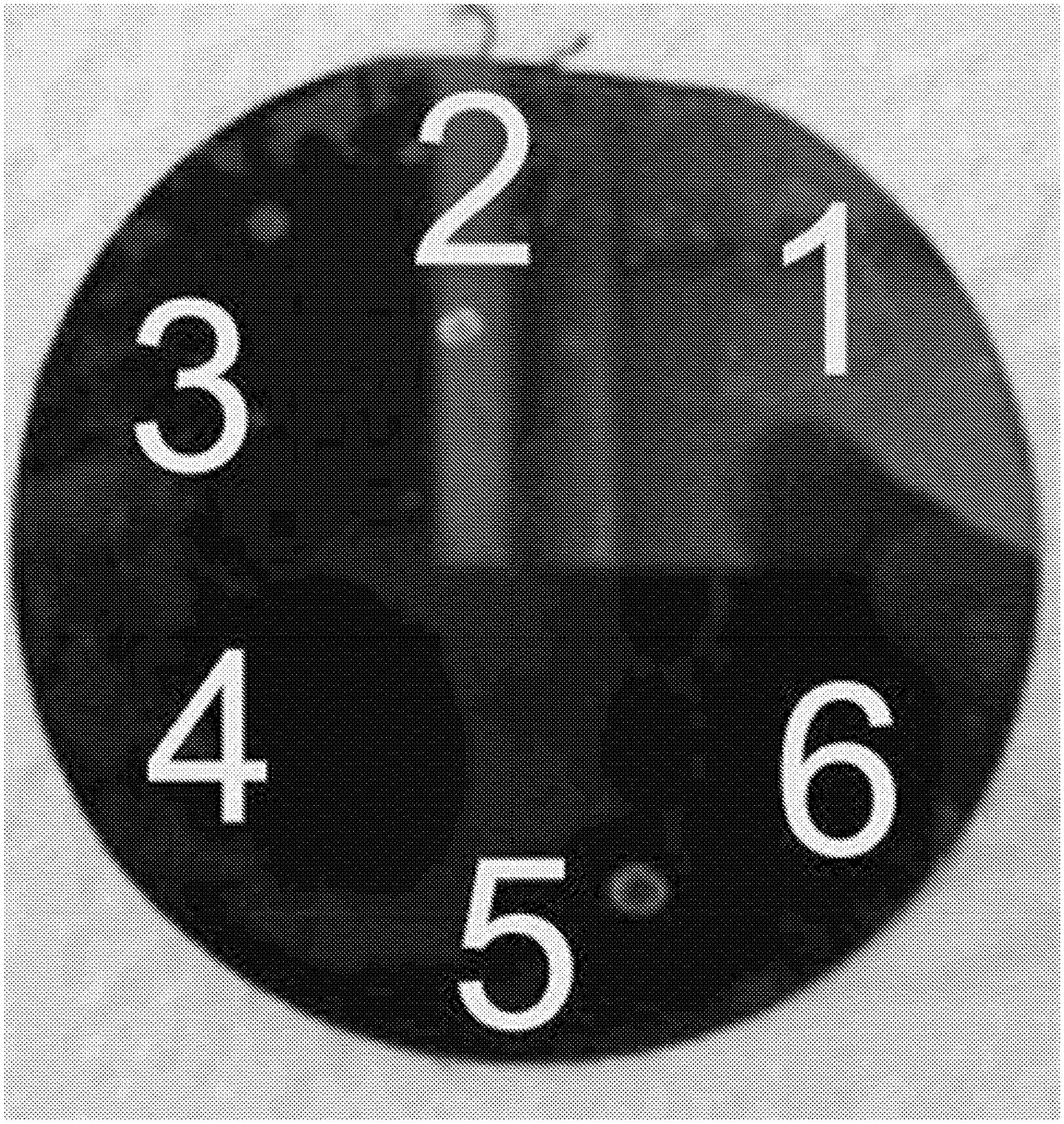
FIG. 3 is an annotated graphical representation of a photograph of an exemplary configuration of a silicon wafer to hold sample(s).

FIG. 3 shows an example of a Silicon wafer with spotted samples (numbered 1-6) on the surface. Each spot is analyzed using the techniques described above. Results described herein were based on measurements made in this manner.

Figure 4:
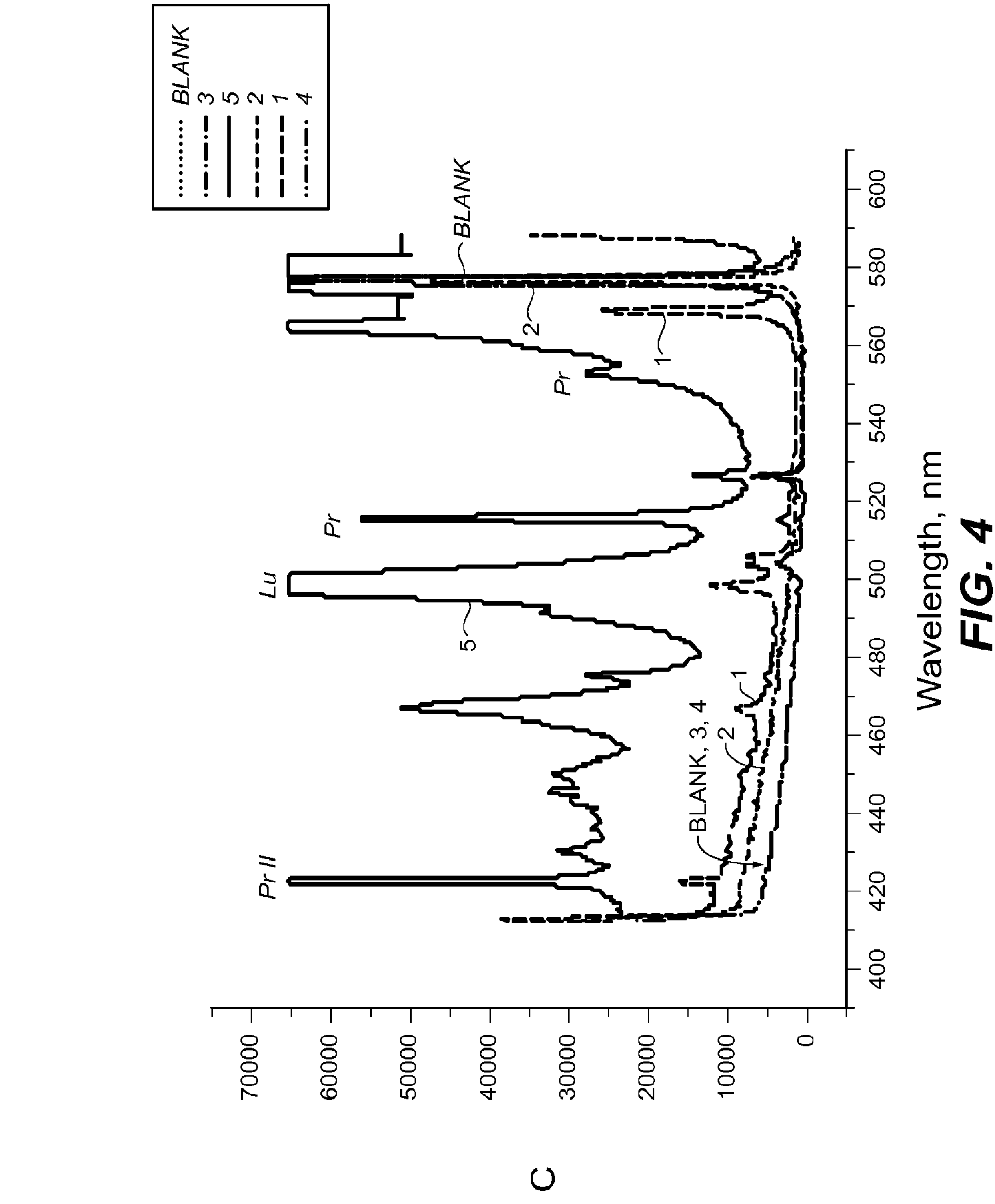
FIG. 4 is a plot showing spectral measurement of a sample containing antitoxin antibodies labeled with Lu and Pr in the 400-600 nm range according to one embodiment.
Figure 5:
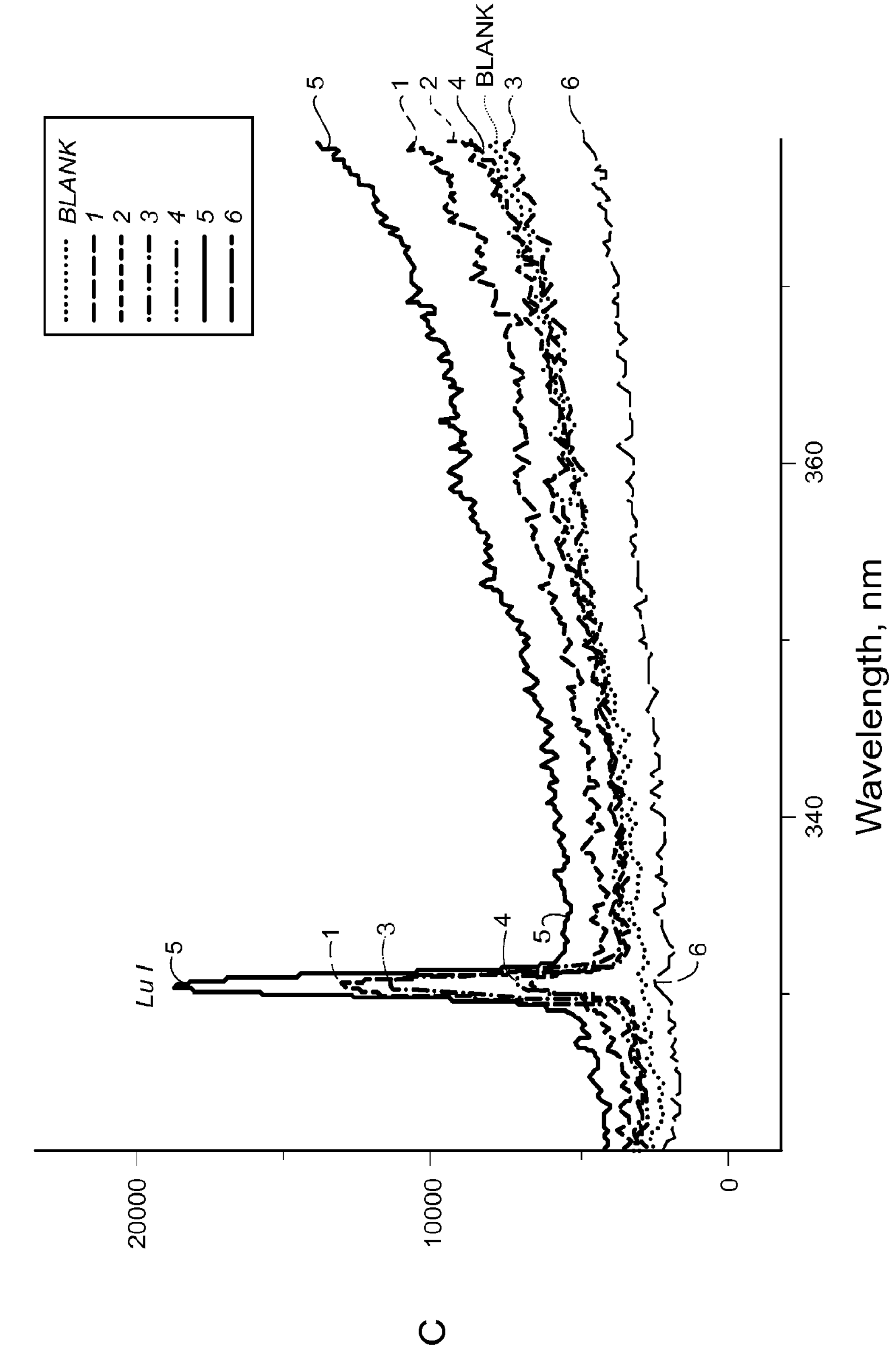
FIG. 5 is a plot showing spectral measurement of a sample containing antitoxin antibodies labeled with Lu and Pr in the 320-380 nm range according to one embodiment.
Figure 6:
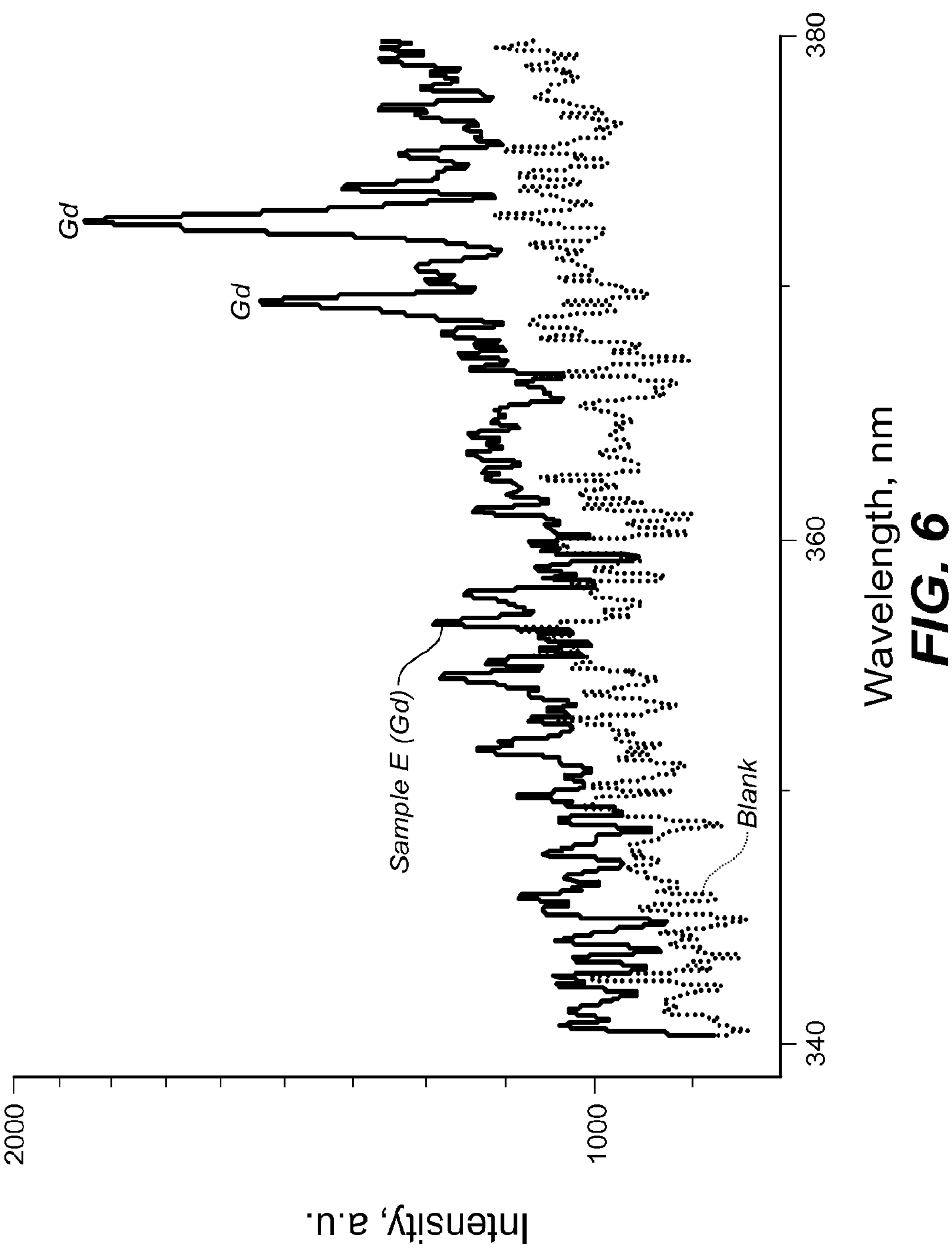
FIG. 6 is a plot showing spectral measurement of a sample containing antitoxin antibodies labeled with Gd 156 and a blank sample in the 340-380 nm range according to one embodiment.
Figure 7:
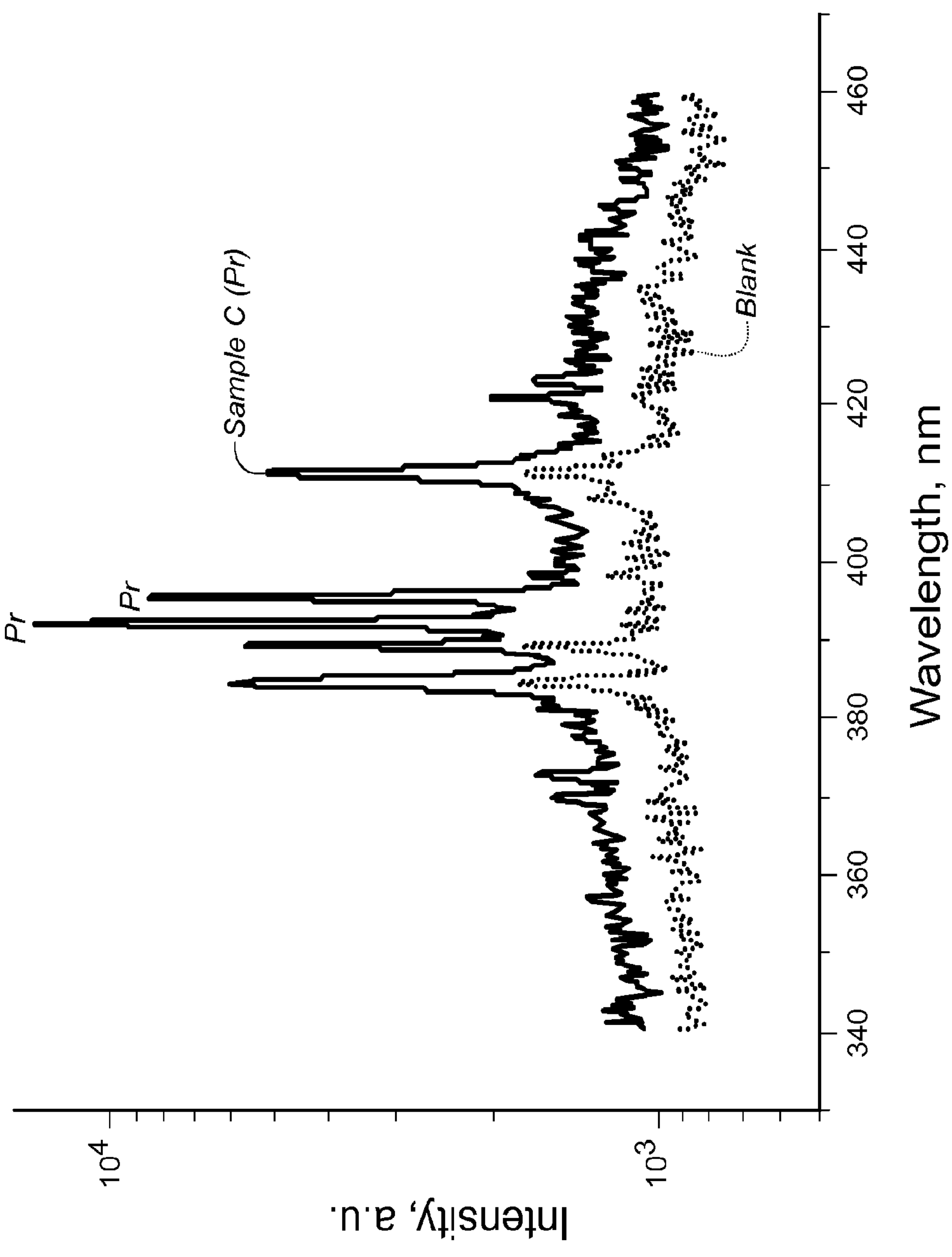
FIG. 7 is a plot showing spectral measurement of a sample containing antitoxin antibodies labeled with Pr in the 340-460 nm range according to one embodiment.
Figure 8:
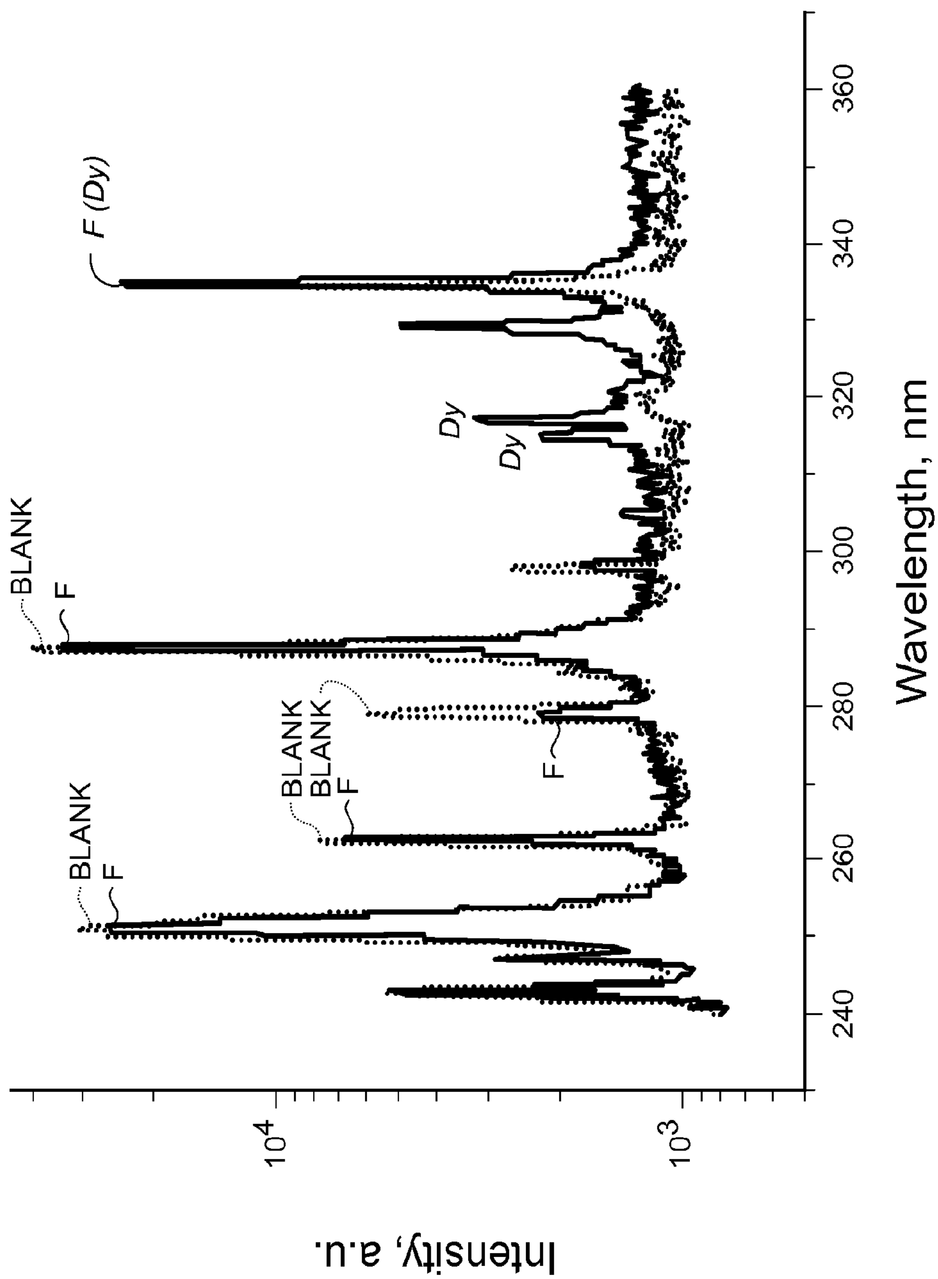
FIG. 8 is a plot showing spectral measurement of a sample containing antitoxin antibodies labeled with Dy in the 240-360 nm range according to one embodiment.
Figure 9:
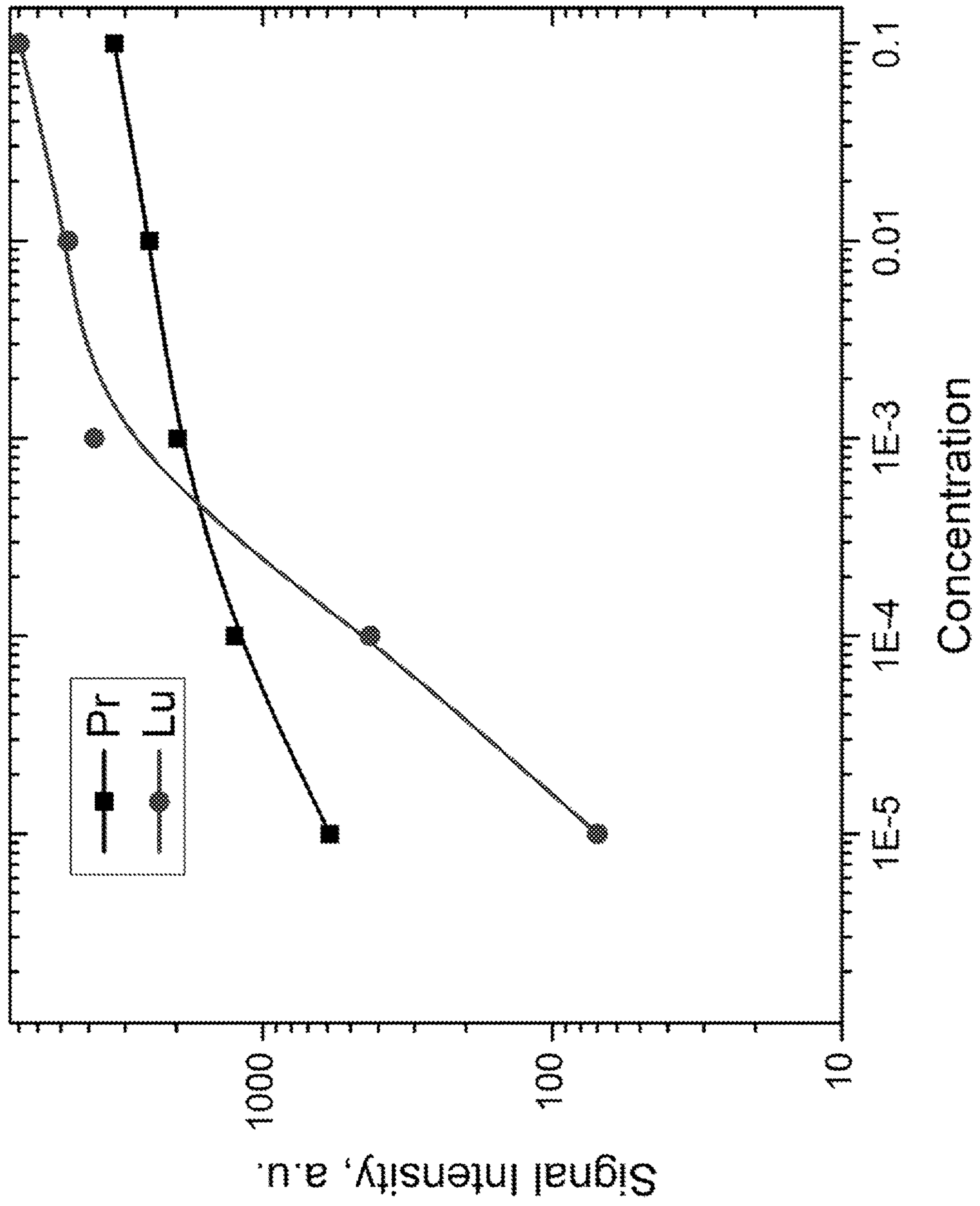
FIG. 9 is a plot showing initial dose response to two different agents, Shiga Toxin Stx-2-2 labeled with Pr 141 and Ricin labeled with Dy 162.
Figure 10:
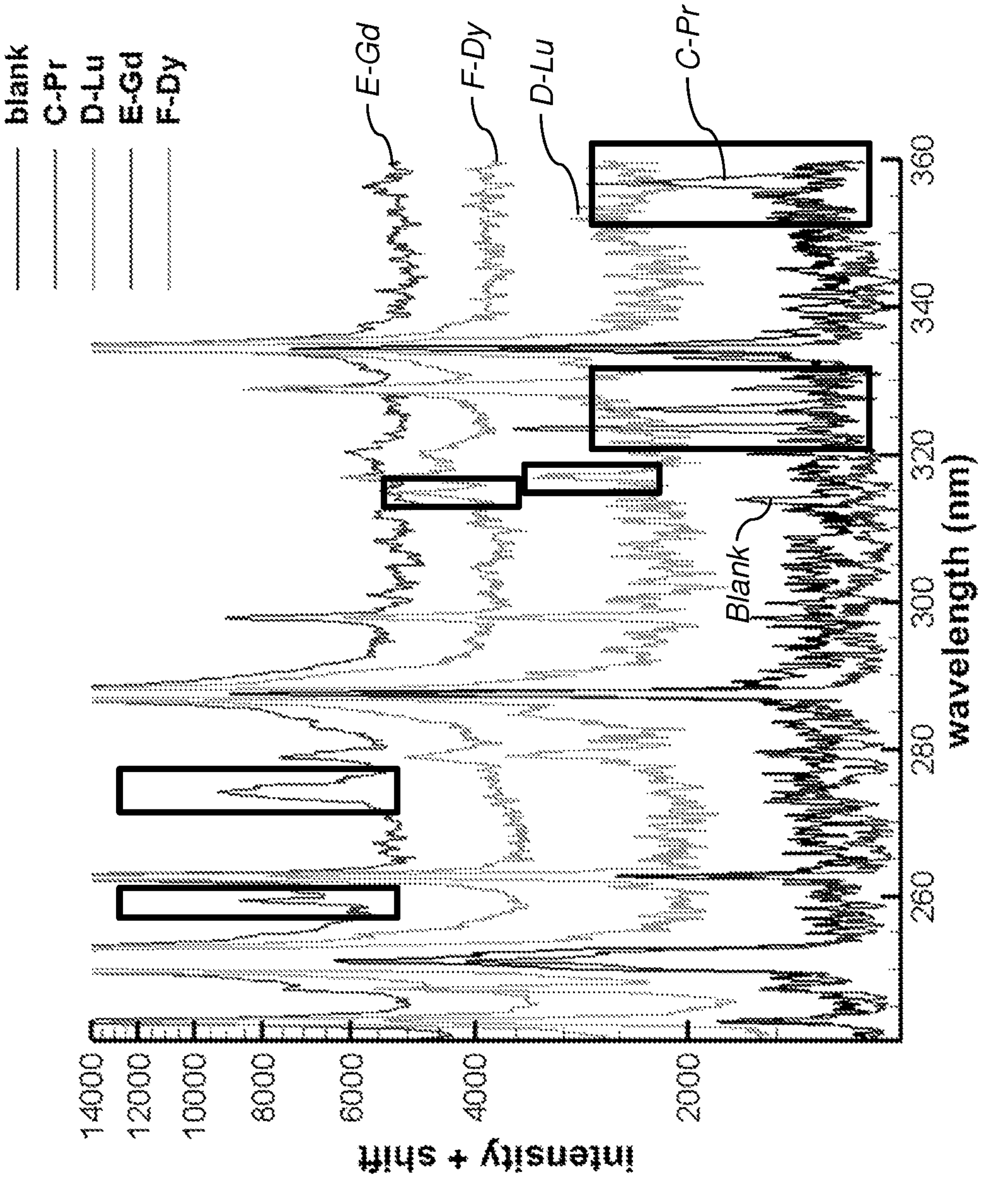
FIG. 10 is a plot showing spectral measurement of the 240 nm-360 nm window, where there are possible peaks that only exists on certain regions of the spectra (for Pr, Lu, Gd, and Dy).

FIG. 4 is a plot showing spectral measurement of a sample containing antitoxin antibodies labeled with Lu and Pr in the 400-600 nm range. FIG. 5 is a plot showing spectral measurement of a sample containing antitoxin antibodies labeled with Lu and Pr in the 320-380 nm range. FIG. 6 is a plot showing spectral measurement of a sample containing antitoxin antibodies labeled with Gd 156 and a blank sample in the 340-380 nm range. FIG. 7 is a plot showing spectral measurement of a sample containing antitoxin antibodies labeled with Pr in the 340-460 nm range. FIG. 8 is a plot showing spectral measurement of a sample containing antitoxin antibodies labeled with Dy in the 240-360 nm range. FIG. 9 is a plot showing initial dose response to two different agents, Shiga Toxin Stx-2-2 labeled with Pr 141 and Ricin labeled with Dy 162. FIG. 10 is a plot showing spectral measurement of the 240 nm-360 nm window, where there peaks can be identified on regions of the spectra representing Pr, Lu, Gd, and Dy simultaneously as shown.

Steps of various methods described herein can be performed in any order except when otherwise specified, or when data from an earlier step is used in a later step. Exemplary method(s) described herein are not limited to being carried out by components particularly identified in discussions of those methods.

In view of the foregoing, various aspects relate to a system for characterizing a biological target within a sample, the system comprising: a. a high energy source; b. a sample container for containment of the sample; c. a recognition scaffold; d. a tag containing a metal element; e. a system for collection of atomic spectra; and f. a system for extracting features from spectra and identifying tags. Various aspects relate to such a system, the biological target comprising microbial samples or biological toxins.

In view of the foregoing, various aspects provide measurement of constituents of a sample. A technical effect of various aspects is to ablate a small quantity of the sample to form a plasma and to measure the constituents of the plasma spectroscopically. A technical effect of various aspects is to provide a metal-labeled target. A further technical effect of various aspects is to present a visual representation of the detected spectra or corresponding abundances of selected biomolecules on an electronic display. This can permit medical or scientific personnel to more readily determine whether a sample contains a target of interest, e.g., at a selected concentration or quantity.

In various embodiments of the method according to the invention can optionally also be made of one and/or other of the following provisions:

According to one aspect, a method for characterizing a biological target within a sample, the method comprising:

labeling the target with a biomolecular recognition construct; and measuring an atomic-spectra signal of the biomolecular recognition construct;

According to another aspect, heating the labeled target before measuring the atomic-spectra signal.

According to another aspect, the atomic-spectra signal is measured by performing laser-induced breakdown spectroscopy.

According to another aspect, the atomic-spectra signal is measured by performing spark induced breakdown spectroscopy.

According to another aspect, data of the atomic-spectra signal is classified using a computer-based classifier and assigning a classification score to the analyzed sample.

According to another aspect, the biomolecular recognition construct is prepared by tagging a biological scaffolding with a metal atom or ion.

According to another aspect, the target includes a microbial sample and the biological scaffolding comprises an antibody against epitopes present on bacterial surface, said antibody linked to a heavy metal.

According to another aspect, the target includes a biological toxin and the biological scaffolding comprises an antibody against the biological toxin linked to heavy metals.

In various embodiments of the apparatus according to the invention can optionally also be made of one and/or other of the following provisions:

According to one aspect, an apparatus for detecting a biological target in a sample, the apparatus comprising:

a. a construct subsystem configured to add a biomolecular recognition construct to the sample;

b. a wash subsystem configured to wash unbound recognition construct out of the sample;

c. a heating subsystem configured to heat the sample-construct mixture so that metals in the biomolecular recognition construct in the washed sample emit photons at characteristic wavelengths; and d. a spectroscopic detector configured to detect light emitted by the metals.

According to one aspect, the heating subsystem includes a laser.

According to one aspect, the heating subsystem includes at least two electrodes and a high-voltage power supply connected to the at least two electrodes and configured to selectively produce a spark across the at least two electrodes.

The invention is inclusive of combinations of the aspects described herein. References to “a particular aspect” (or “embodiment” or “version”) and the like refer to features that are present in at least one aspect of the invention. Separate references to “an aspect” (or “embodiment”) or “particular aspects” or the like do not necessarily refer to the same aspect or aspects; however, such aspects are not mutually exclusive, unless otherwise explicitly noted. The use of singular or plural in referring to “method” or “methods” and the like is not limiting. The word “or” is used in this disclosure in a non-exclusive sense, unless otherwise explicitly noted.

The invention has been described in detail with particular reference to certain preferred aspects thereof, but it will be understood that variations, combinations, and modifications can be effected within the spirit and scope of the invention.

The invention claimed is:

1. A system for characterizing a target within a sample, the system comprising:

the sample, wherein the sample comprises:

a molecular recognition scaffold configured to couple with the target;

a polymer coupled to the molecular recognition scaffold and comprising a metal-chelating ligand; and a first metal atom or ion linked to the metal-chelating ligand;

a laser to generate a plasma of the first metal atom or ion in the sample;

an optical spectroscopic detector configured to detect electromagnetic radiation emitted by the plasma and to provide an atomic-spectra signal corresponding to at least some of the electromagnetic radiation; and a substrate comprising recognition macromolecules bound to a surface, the recognition macromolecules being configured to retain the sample in operative arrangement with the laser by coupling with the target.

2. The system according to claim 1, further comprising:

a processor; and a processor-accessible memory storing instructions executable by the processor to cause the processor to perform operations comprising:

determining presence of the target in the sample by determining presence of the first metal atom or ion in the sample based at least in part on the atomic-spectra signal, the target being a biological toxin.

3. The system according to claim 2, the operations further comprising:

performing spectral unmixing or spectral fingerprint classification on the atomic-spectra signal.

4. The system according to claim 2, the operations further comprising:

determining presence of a second metal atom or ion in the sample based at least in part on the atomic-spectra signal, wherein the second metal atom or ion is different from the first metal atom or ion.

5. The system according to claim 1, wherein the substrate comprises a silicon wafer.

6. The system according to claim 1, wherein the molecular recognition scaffold comprises at least one of an antibody, adNectin, iMab, anticalin, microbody, peptide aptamer, designed ankyrin repeat protein (DARPin), affilin, tetranectin, or avimer.

7. The system according to claim 1, further comprising:

a construct subsystem configured to add a recognition construct to the sample, the recognition construct comprising the molecular recognition scaffold and the first metal atom or ion; and a wash subsystem configured to form a washed sample by washing unbound recognition construct out of the sample.

8. The system according to claim 1, wherein the molecular recognition scaffold-comprises an antitoxin antibody.

9. The system according to claim 1, wherein the molecular recognition scaffold comprises an antibody against at least one epitope present on a surface of a microbe.

10. A method using the system of claim 7, the method comprising:

applying to the sample, by the construct subsystem, the recognition construct comprising the first metal atom or ion and the molecular recognition scaffold;

generating, by the laser, the plasma of at least some of the sample; and detecting, by the optical spectroscopic detector, the electromagnetic radiation emitted by the plasma to provide the atomic-spectra signal of the sample.

11. The method according to claim 10, wherein the generating comprises heating at least part of the sample.

12. The method according to claim 10, wherein the generating comprises irradiating at least part of the sample using the laser.

13. The method according to claim 10, further comprising:

determining, by a processor, presence of the first metal atom or ion in the sample based at least in part on the atomic-spectra signal by performing at least spectral unmixing or constrained energy minimization (CEM).

14. The method according to claim 10, further comprising:

preparing, by the construct subsystem, the recognition construct by bonding the first metal atom or ion to the molecular recognition scaffold, wherein the molecular recognition scaffold comprises a biological scaffold.

15. The method according to claim 10, wherein the target comprises a microbe and the molecular recognition scaffold comprises a biological toxin.

16. A system for characterizing a target within a sample, the system comprising:

the sample, wherein the sample comprises:

a molecular recognition scaffold configured to couple with the target;

a polymer coupled to the molecular recognition scaffold and comprising a metal-chelating ligand; and a first metal atom or ion linked to the metal-chelating ligand;

a power supply;

at least two electrodes connected to the power supply and configured to generate a plasma of the first metal atom or ion in the sample;

an optical spectroscopic detector configured to detect electromagnetic radiation emitted by the plasma and to provide an atomic-spectra signal corresponding to at least some of the electromagnetic radiation; and a substrate comprising recognition macromolecules bound to a surface, the recognition macromolecules being configured to retain the sample in operative arrangement with the laser by coupling with the target.

17. The system according to claim 16, further comprising:

a processor; and a processor-accessible memory storing instructions executable by the processor to cause the processor to perform operations comprising:

performing spectral unmixing or spectral fingerprint classification on the atomic-spectra signal;

determining presence of the target in the sample by determining presence of the first metal atom or ion in the sample based at least in part on the atomic-spectra signal, the target being a biological toxin; and determining presence of a second metal atom or ion in the sample based at least in part on the atomic-spectra signal, wherein the second metal atom or ion is different from the first metal atom or ion.

18. The system according to claim 16, wherein the substrate comprises a silicon wafer.

19. The system according to claim 16, wherein the first antibody comprises an antitoxin antibody.

20. The system according to claim 16, wherein the power supply is a high voltage power supply connected to the two electrodes and configured to selectively produce a spark across the two electrodes.

* * * * *